United States Patent [19]
Makriyannis et al.

[11] Patent Number: 6,166,066
[45] Date of Patent: Dec. 26, 2000

[54] CANNABINOIDS SELECTIVE FOR THE CB2 RECEPTOR

[75] Inventors: Alexandros Makriyannis, Willimantic; Atmaram Khanolkar; Dai Lu, both of Storrs, all of Conn.

[73] Assignee: The University of Connecticut, Farmington, Conn.

[21] Appl. No.: 09/304,718

[22] Filed: May 4, 1999

Related U.S. Application Data

[60] Provisional application No. 60/084,129, May 4, 1998.

[51] Int. Cl.$^7$ .................................................. A61K 31/35
[52] U.S. Cl. ........................ 514/453; 549/280; 549/383; 549/384
[58] Field of Search ............................ 514/453; 549/383, 549/384, 280

[56] References Cited

U.S. PATENT DOCUMENTS

| | | | |
|---|---|---|---|
| 3,886,184 | 5/1975 | Matsumoto et al. | 260/345.3 |
| 3,915,996 | 10/1975 | Wright et al. | 260/345.3 |
| 5,440,052 | 8/1995 | Makriyannis et al. | 549/390 |
| 5,688,825 | 11/1997 | Makriyannis et al. | 514/423 |
| 5,872,148 | 2/1999 | Makriyannis et al. | 514/454 |
| 5,874,459 | 2/1999 | Makriyannis et al. | 514/425 |

FOREIGN PATENT DOCUMENTS

| | | | |
|---|---|---|---|
| 0276732 A2 | 1/1988 | European Pat. Off. | C07D 311/80 |
| 2 240 003 | 3/1975 | France | A61K 31/35 |
| 2735774 A1 | 6/1995 | France | C07D 295/096 |
| WO 99/57106 | 11/1999 | WIPO | C07D 311/80 |
| WO 99/57107 | 11/1999 | WIPO | C07D 311/80 |

OTHER PUBLICATIONS

Pitt et al., "The Synthesis of Deuterium, Carbon–14, and Carrier–Free Tritium Labeled Cannabinoids",*Journal of Labelled Compounds*, 11(4) :551–575 (1975).

Huffman et al., "Synthesis of a Tetracyclic, Conformationally Constrained Analogue of $\Delta^8$–THC", *Bioorganic & Medicinal Chemistry*, 6(12):2281–2288 (1998).

Mavromoustakos, T., et al., "Studies on the termotropic effects of cannabinoids on phosphatidylcholine bilayers using differential scanning calorimetry and small angle X–ray diffraction", *Biochimica et Biophysica Acta*, 1281 (2) :235–244 (1996).

Fahrenholtz, K.E., "The Synthesis of Two Metabolities of (–)–$\Delta^8$–Tetrahydrocannabinol", *J. Org. Chem.*, 37 (13):2204–2207 (1972).

Matsumoto, K., et al., "Cannabinoids. 1. 1–Amino–and 1–Mercapto–7,8,9,10–tetrahydro–6H–dibenzo[b,]pyrans", *J. of Med. Chem.*, 20(1):17–24 (1977).

Smith, P. B., et al., "The Pharmacological Activity of Anandamine, a Putative Endogenous Cannabinoid, in Mice", *Journal of Pharmacology and Experimental Therapeutics*, vol. 270(1):219–227 (1994).

Crawley, J. N., et al., "Anandamine, an Endogenous Ligand of the Cannabinoid Receptor, Induces Hypomotility and Hypothermia In Vivo in Rodents", *Pharmacology Biochemistry and Behavior*, vol. 46:967–972 (1993).

Fride, E. and Mechoulam, R., "Pharmacological activity of the cannabinoid receptor agonist, anandamide, a brain constituent," *European Journal of Pharmacology*, vol. 231:313–314 (1993).

Mechoulam, Cannabinoids as Therapeutic Agents, CRC Press, Boca Raton, FL (1986).

Barnett–Norris, J., et al., "Exploration of Biologically Relevant conformations of Anandamine, 2–Arachidonylglycerol, and Their Analogues Using Conformation Memories," *J. Med. Chem.*, vol. 41:4861–4872 (1998).

Razdan, R.K, et al., Caplus abstract of "Drugs Delivered From Cannabinoids. 6. Synthesis of Cyclic Analogues of Dimethylheptylpyran," *J. Med. Chem.* vol. 19(5):719–721 (1976), CA 84:144578, cited by the Examiner.

Belgaonkar, V., et al., Caplus abstract of "Synthesis of Isocoumarins," *Indian J. Chem.* vol. 13(4):336–338 (1975), CA 83:96937, cited by the Examiner.

Falbe J. and Regitz M., Römpp Chemie Lexikon, "Band 1–A–C1, 8," *Aufl, Thieme Verlag*, Stuttgart, S 569–570 (1989).

Razdan, R.K. et al "Drugs Derived from Cannabinoids. 6. Synthesis of Cyclic Analogues of dimethylheptylpyran" CA 84:144578 (1976).

Belganokar, V.H. et al "Isocoumarins, XIV, Synthesis of 3–Benzylissocoumarins and 3–Benzyl–1(2H)–Isoquinolines" CA 83:96937 (1975).

Primary Examiner—Amelia Owens

[57] ABSTRACT

Disclosed are novel cannabinoids which are selective for the CB2 receptor. The novel cannabinoids comprise a substituted or unsubstituted tricyclic cannabinoid core and a substituted or unsubstituted C5–C8 carbocyclic ring, five to eight-membered heterocyclic ring or a seven to ten membered bicyclic ring system fused to the monhydroxylated phenyl ring of the cannabinoid core. Also disclosed are methods of suppressing the immune system in a subject by administering to the subject a (e.g. immunosuppressive amount) effective amount of a novel cannabinoid described above.

16 Claims, 7 Drawing Sheets

Scheme 1

Scheme 2

FIGURE 2

Scheme 3

Figure 3

Scheme 4

CANNABINOIDS SELECTIVE FOR THE CB2 RECEPTOR

RELATED APPLICATION

This application claims the benefit of U.S. Provisional Application No. 60/084,129, filed May 4, 1998, the contents of which are incorporated herein by reference in their entirety.

GOVERNMENT SUPPORT

The invention was supported, in whole or in part, by grants DA3801 and DA9158 from the National Institute of Drug Abuse (NIDA). The Government has certain rights in the invention.

BACKGROUND OF THE INVENTION $\Delta^8$-Tetrahydrocannabinol, the pyschoactive marijuana derived cannabinoid, binds to the CB1 receptor in the brain and to the CB2 receptor in the spleen. Activation of the CB2 receptor has been shown to result in suppression of the immune system (Mechoulam, *Cannabinoids as Therapeutic Agents*, CRC Press, Boca Raton, Fla. (1986)). Thus, drugs which selectively activate the CB2 receptor have great potential as immunomodulatory agents for preventing tissue rejection in organ transplant patients and as immunosuppressive agents for treating autoimmune associated diseases, (e.g., lupus erythematosus, rheumatoid arthritis, psoriasis, multiple sclerosis and inflammatory bowel diseases such as ulcerative colitis and Crohn's disease). CB2 receptor agonists also can be used as anti-inflammatory agents and as agents for suppressing peripheral and idiopathic pain.

Unfortunately, most known CB2 receptor agonists, including most cannabinoids, are non-selective in that they also stimulate the CB1 receptor. Activation of the CB1 receptor causes the sedative and pyschotropic effects which are associated with marijuanna use. As a consequence, there are few if any agents which can target the CB2 receptor without at the same time causing these undesirable side-effects. The full potential of therapies which modulate the immune system by selectively stimulating the CB2 receptor is unlikely to be realized without the further development of agents which are selective agonists of the CB2 receptor.

SUMMARY OF THE INVENTION

Reported herein are novel compounds which selectively activate the CB2 receptor. These compounds are cannabinoids in which the alkyl side chain typically found in cannabinoids has been replaced with a monocyclic or bicyclic ring that is fused to the tricyclic core typically found in cannabinoids. For example, the affinity of AM724 for the CB2 receptor was found to be about 400 times greater than for the CB1 receptor (Example 2). The structure of AM724 is shown below along with $\Delta^8$-tetrahydrocannabinol.

AM724

Delta-8-Tetrahydrocannabinol

Based on these results, novel compounds which are selective CB2 receptor agonists and the use of these compounds for modulating the immune system in a subject are disclosed.

One embodiment of the present invention is a compound comprising a substituted or unsubstituted tricyclic cannabinoid core. The cannabinoid core comprises a phenyl ring and a six-membered carbocyclic ring fused to a central pyran ring or to a central six-membered lactone ring (preferably a pryan ring). A substituted or unsubstituted C5–C8 carbocyclic ring, a five to eight-membered heterocyclic ring or a seven to ten membered bicyclic ring is fused to the phenyl ring. Also included are physiologically acceptable salts of the compound.

Another embodiment of the present invention is a method of suppressing the immune system in a subject. The method comprises administering to the subject a therapeutically effective amount of a compound comprising a substituted or unsubstituted tricyclic cannabinoid core. The cannabinoid core comprises a phenyl ring and a six-membered carbocyclic ring fused to a central pyran ring or to a central six-membered lactone ring (preferably a pryan ring). A substituted or unsubstituted C5–C8 carbocyclic ring, a five to eight-membered heterocyclic ring or a seven to ten membered bicyclic ring is fused to the phenyl ring.

The compounds of the present invention are effective in stimulating the CB2 receptor without substantially activating the CB1 receptor. Thus, the compounds of the present invention can suppress the immune system in subjects without causing the psychotropic and sedative side-effects which are characteristic of cannabinoids such as $\Delta^8$-tetrahydrocannabinol. These compounds are therefore useful as drugs for suppressing organ transplant rejection, for treating autoimmune diseases (e.g., lupus erythematosus, rheumatoid arthritis, psoriasis, multiple sclerosis and inflammatory bowel disease such as ulcerative colitis and Crohn's disease), for treating inflammation, and for suppressing peripheral and idiopathic pain. In addition, the compounds of the present invention are likely to cause no more than minimal side-effects.

DETAILED DESCRIPTION OF THE INVENTION

Cannabinoids have a core tricyclic ring system in which a phenyl ring and a six membered ring are each fused to a central pyran ring or to a six-membered lactone ring (preferably a pyran ring). In addition, cannabinoids are able to induce characteristic physiological effects in mammals, including euphoria, delerium, drowsiness, hallucinations, weakness and/or hyporeflexia. The tricyclic core found in some cannabinoids is shown in Structural Formula (I). Other cannabinoids have the tricyclic core shown in Structural Formula (I), modified to include one or more double bonds in Ring A, for example, a double bond between carbons 8 and 9, between carbons 9 and 10 or between carbons 9 and 11. Yet other cannabinoids have the core structures described above, modified to include hydrogen, hydroxyl, hydroxymethyl, halogen (chloro, bromo, iodo and fluoro), methoxy, ethoxy, nitrile, nitro, halogenated methyl, halogenated ethyl, methoxymethyl, ethoxymethyl, nitromethyl, ethyl or —$CH_2CN$ group bonded to carbon 11 instead of a methyl group. In other cannabinoids, the hydroxyl group at position 1 of the core structure is replaced, for example, with —H, —$OCH_3$, —$NH_2$ or —$NHCH_3$. The term "tricyclic cannabinoid core", as it is used herein, also refers to structures which are 1) related to Structural Formula (I); and (2) found in compounds which induce one or more of the physiological effects described above that are characteristic of the cannabinoids. Also shown in Structural Formula (I) is a numbering system for the ring atoms in the core tricylic structure.

(I)

Cannabinoids also generally substituted with a linear alkyl side chain at position C-3 of the cannabinoid core. In the cannabinoids of the present invention, the linear alkyl side chain is replaced with a substituted or unsubstituted C5–C8 carbocyclic ring, a five to eight-membered heterocyclic ring or a seven to ten membered bicyclic ring fused to positions two and three of the cannabinoid core.

Suitable substituents for a tricyclic cannabinoid core include groups which do not significantly diminish the ability of a cannabinoid to activate a cannabinoid receptor. Substitutions can occur at positions 2, 4, 6a–10a or at the three methyl groups. Substitution(s) at more than one position are possible. Substituents which do not significantly diminish the biological activity of cannabinoids are generally small, pharmacophoric groups. Examples include —H, —OH, —$OCH_3$, —$OCH_2CH_3$, halogen (e.g., chloro, bromo, iodo and fluoro), —CN, azido, isocyanate, isothiocyanate, —$NO_2$, —$CH_3$, —C(halogen)$_3$, —$CH_2OH$, —$CH_2OCH_3$, —$CH_2OCH_2CH_3$, —$CH_2$(halogen), —$CH_2CN$, —$CH_2NO_2$, —$CH_2CH_3$ and —$CH_2C$(halogen)$_3$. Cannabinoids with other substituents can be prepared by modification of the synthetic procedures described in Example 1 and shown in FIGS. 2–4. For example, replacing the alcohol which reacts with compound 4 in Scheme 1 of FIG. 2 with a suitably substituted analog results in the preparation of cannabinoids with a substituted cyclohexene ring or with substituents on one of the methyl groups attached to the pyran or cyclohexene ring. Other suitable substituents can be identified by testing modified cannabinoids in the in vitro CB1 or CB2 assays described in Example 2.

Two rings are fused when they share one single bond, one double bond or two adjacent ring atoms. For example, a cyclohexane ring fused to a phenyl ring forms a tetrahydronaphthalene group; a cyclopentane ring fused to a phenyl ring forms an indane group. In the present invention, the phenyl ring of the cannabinoid core is fused to a substituted or unsubstituted C5–C8 carbocyclic, a C5–C8 non-aromatic heterocyclic ring or to a seven to ten membered bicyclic ring.

Carbocyclic rings are non-aromatic rings which include only carbon as ring atoms. Examples include substituted or unsubstituted cyclopentane, cyclohexane, cycloheptane and cyclooctane.

Heterocyclic rings are non-aromatic rings which have one or more heteroatoms, including oxygen, nitrogen and/or sulfur, as ring atoms. Examples of suitable heterocyclic rings include substituted or unsubstituted tetrahydrofuran, tetrahyrothiophene, 1,4-dioxane, morpholine, thiomorpholine, pyrrolidine, pyran, piperazine, piperidine and thiazolidine.

Bicyclic ring systems contain two non-aromatic rings which are bridged or fused. Optionally, a bicyclic ring can have one or more heteroatoms such as oxygen, sulfur or nitrogen. An example of a suitable fused ring system is decalin. Bridged bicyclic rings share at least three ring atoms and therefore also share at least two single bonds or one single bond and one double bond. Examples of bicyclic structures include a 2.2.1 seven-membered bicyclic structure, a 3.2.1 eight-membered bicyclic structure, a 3.3.1 nine-membered bicyclic structure, a 2.2.2 eight-membered structure and a 3.3.2 nine-membered structure. The structures of carbocyclic 2.2.1 seven membered, a 3.2.1 eight-membered bicyclic, a 3.3.1 nine-membered bicyclic, a 2.2.2 eight-membered and a 3.3.2 nine-membered ring are provided by Structural Formulas (II)–(VI):

-continued (IV)

(V)

(VI)

The nomenclature for bicyclic ring systems indicates the number of rings atoms between bridgeheads. A "bridgehead" is an atom shared by both rings. For example, bicyclo 2.2.1. heptane, shown in Structural Formula (II), has two (C-2 and C-3), two (C-5 and C-6) and one (C-7) carbons between the bridgeheads (C-1 and C-4)

Suitable substituents for the fused carbocyclic, heterocyclic rings and bicyclic ring systems are generally C1–C8 alkyl groups, C1–C8 substituted alkyl groups or small, pharmacophoric groups. Examples of small pharmacophoric groups include, but are not limited to, —H, —OH, —OCH$_3$, —OCH$_2$CH$_3$, halogen (e.g., chloro, bromo, iodo and fluoro), —CN, azido, isocyanate, thioisocyanate, —NO$_2$, —CH$_3$, —C(halogen)$_3$, or —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ and —CH$_2$C(halogen)$_3$. Alkyl groups can be straight chained or branched. Suitable substituents for an alkyl group include small, pharmacophoric groups, as described above.

In a preferred embodiment, the selective CB2 agonist of the present invention is represented by Formula (VII):

(VII)

Ring A has zero, one or two endocyclic double bonds. An "endocyclic double bond" is defined to be a double bond formed between two carbon atoms in a ring. In one example, Ring A has three double bonds. In another example, Ring A has a double bond between carbons 8 and 9. In another example, Ring A has a double bond between carbons 9 and 10. In yet another example, Ring A has no double bonds.

X is >C(CH$_3$)$_2$ or —C=O. X is preferably >C(CH$_3$)$_2$.

R$_1$ is —H, —OH, —OCH$_3$, —OCH$_2$CH$_3$, halogen (chloro, bromo, iodo and fluoro), —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ or —CH$_2$C(halogen)$_3$. R$_1$ in Structural Formula (VII) is preferably —H or —OH.

R$_2$ and R$_3$, taken together with the carbon atoms to which they are bonded, form a substituted or unsubstituted C5–C8 monocyclic or C7–C10 bicyclic carbocyclic ring.

In a more preferred embodiment, the selective CB2 agonist of the present invention is represented by Formula (VIII):

(VIII)

R$_1$ is —CH$_3$ or —CH$_2$OH.

R$_4$–R$_7$ are independently —H or a C1 to C10 straight chained substituted or unsubstituted alkyl group. R$_4$ and R$_5$ are preferably —H or —CH$_3$.

In addition, R$_6$ and R$_7$, taken together, form a substituted or unsubstituted alkylene group, for example, an ethylene, propylene or —(CH$_2$)$_4$— group. Suitable substituents for an alkylene group are as described for a carbocyclic or bicyclic ring.

In an even more preferred embodiment, the selective CB2 agonist of the present invention is represented by Formula (IX):

(IX)

R$_1$, R$_4$ and R$_5$ are as described for Structural Formula (VIII). R$_8$ is a substituted or unsusbstituted C1–C4 alkyl group, preferably a methyl group.

Specific examples of the compounds of the present invention are shown in FIGS. 1 and 5A–5C.

In another preferred embodiment, the selective CB2 agonist of the present invention is represented by Formula (VII), (VIII) or (IX), modified so that the hydroxyl group attached to the phenyl ring is replaced with an —H.

A "therapeutically effective amount" is the quantity of compound which results in immune system suppression in a subject after administration of the compound. Typically, a "therapeutically effective amount" of the compound ranges from about 10 mg/day to about 1000 mg/day, preferably from about 50 mg/day to about 500 mg/day. The specific dosage level of active ingredient will depend upon a number of factors, including, for example, biological activity of the particular preparation, age, body weight, sex and general health of the subject being treated.

As used herein, a "subject" refers to a human or animal. An "animal" refers to veterinary animals, such as dogs, cats, horses, and the like, and farm animals, such as cows, pigs, guinea pigs and the like.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions.

Figure 1:
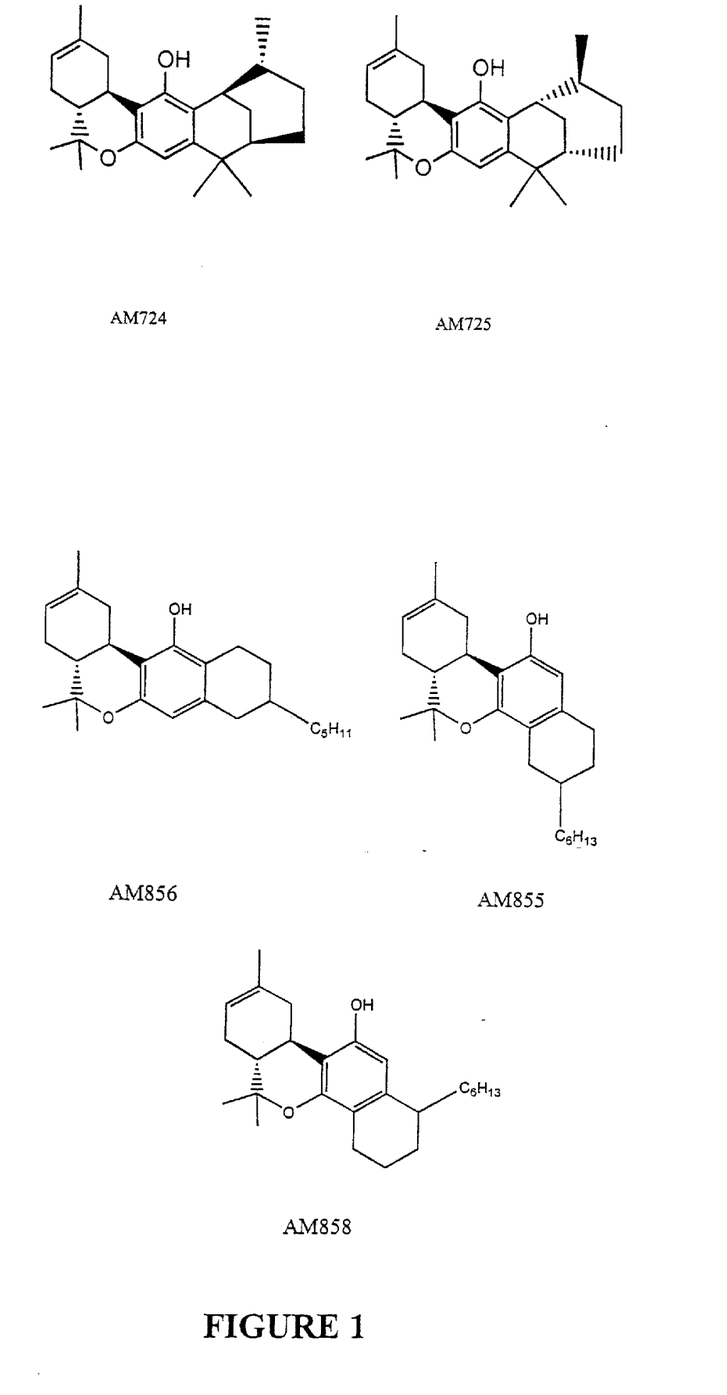
FIG. 1 shows the structure of a number of the novel compounds of the present invention.
Figure 2:
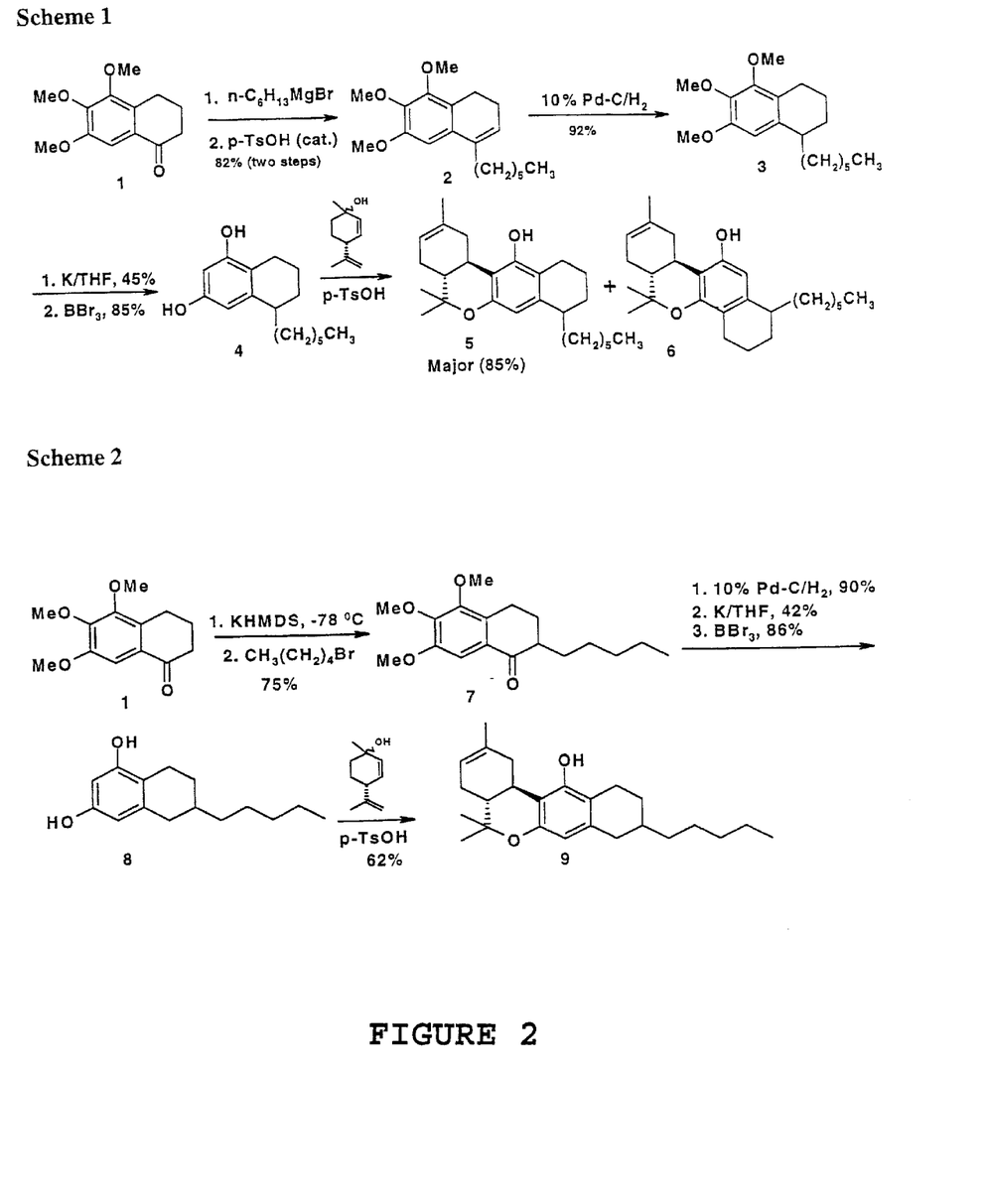
FIG. 2 is a schematic showing two synthesis of (−)-$\Delta^8$-tetrahydrocannabinol and cannabinol analogs with cyclic side chains.
Figure 3:
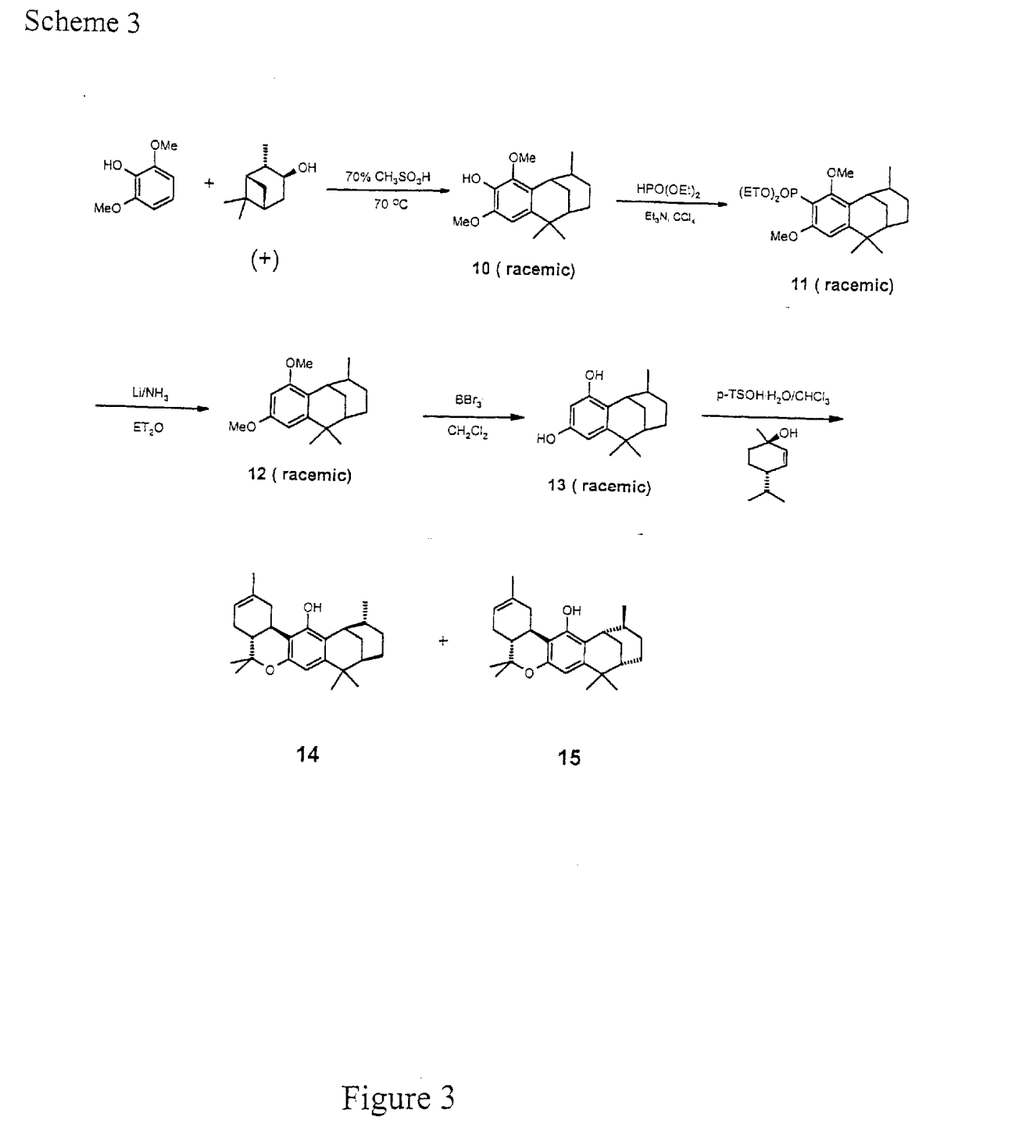
FIG. 3 is a schematic showing two synthesis of (-)-$\Delta^8$-tetrahydrocannabinol and cannabinol analogs with a bridged bicyclic side chains.
Figure 4:
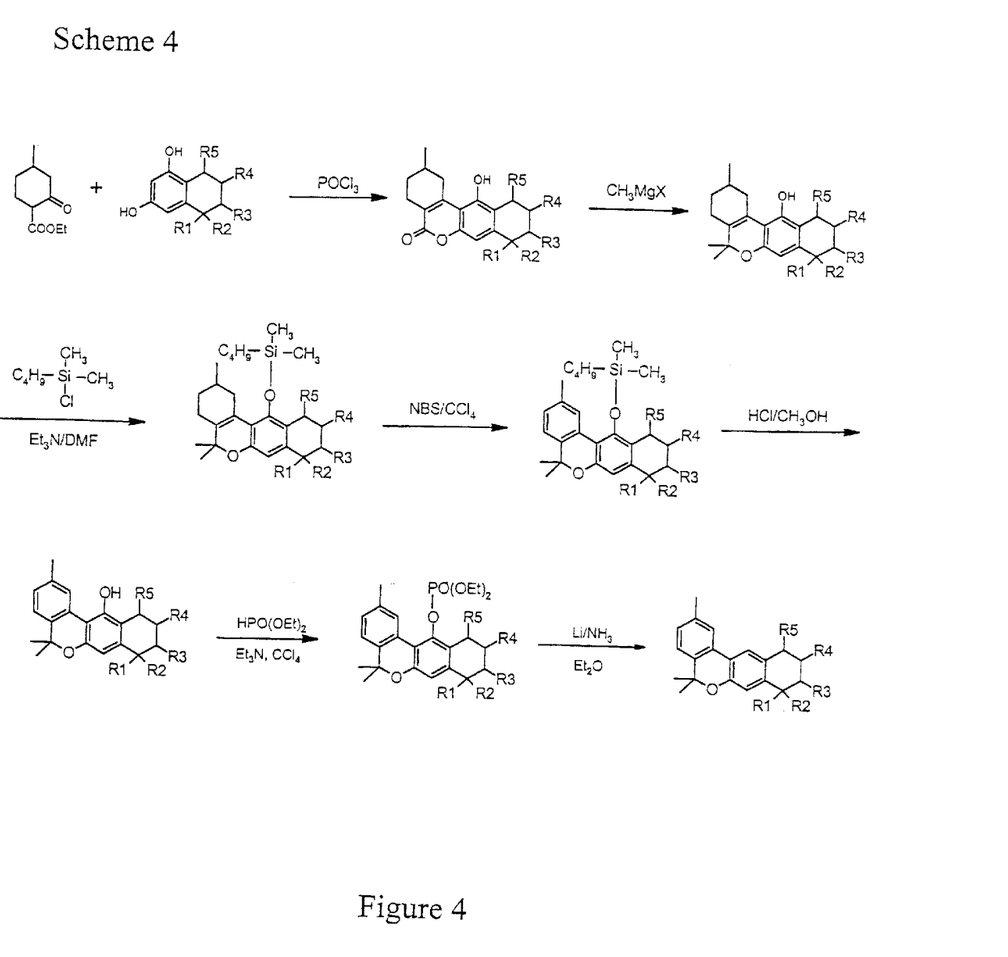
FIG. 4 is a schematic showing a synthesis of (-)-$\Delta^8$-tetrahydrocannabinol and cannabinol analogs with substituted cyclic side chains.
Figure 5A:
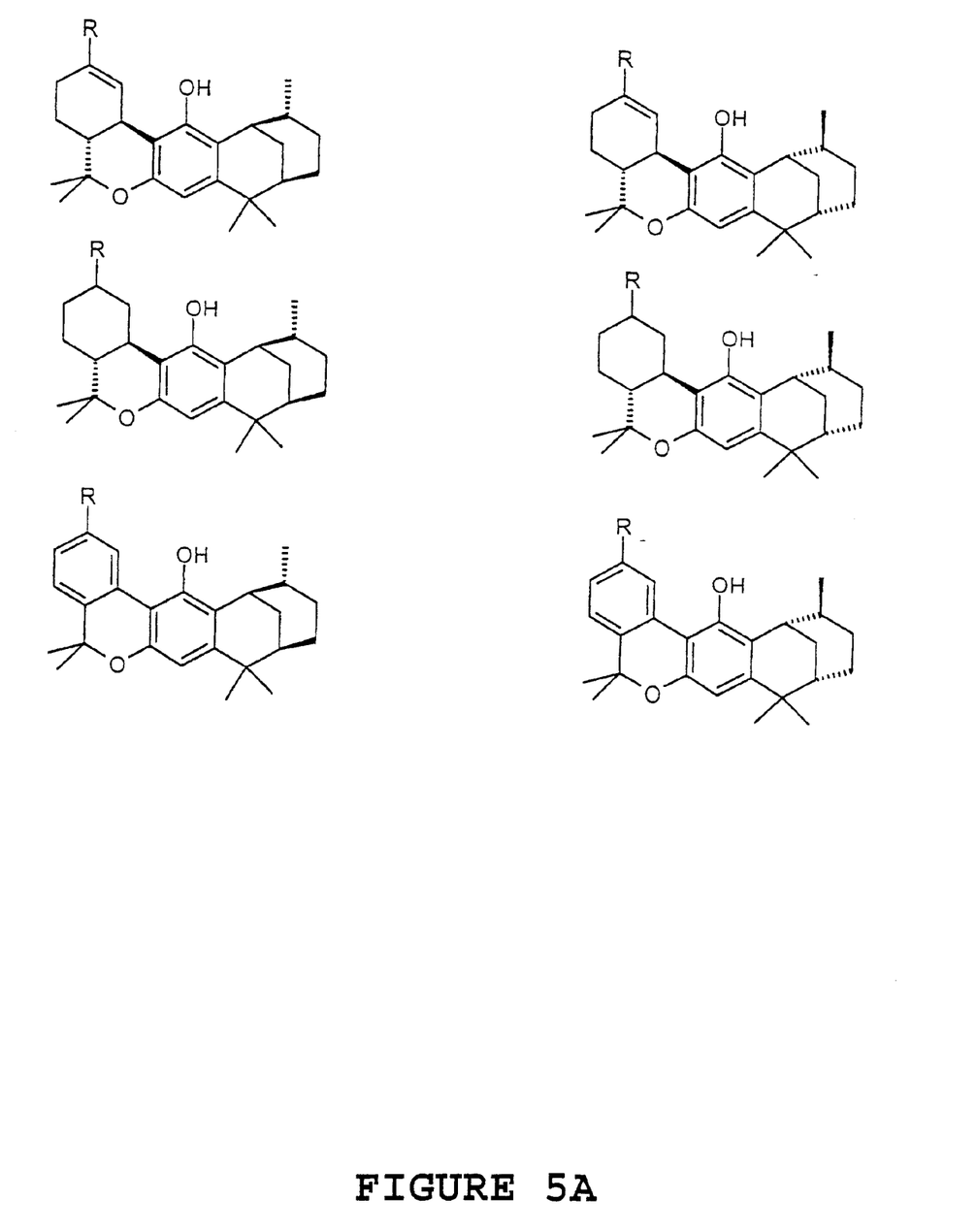
FIGS. 5A, 5B and 5C show the structure of a number of the novel compounds of the present invention.
Figure 5B:
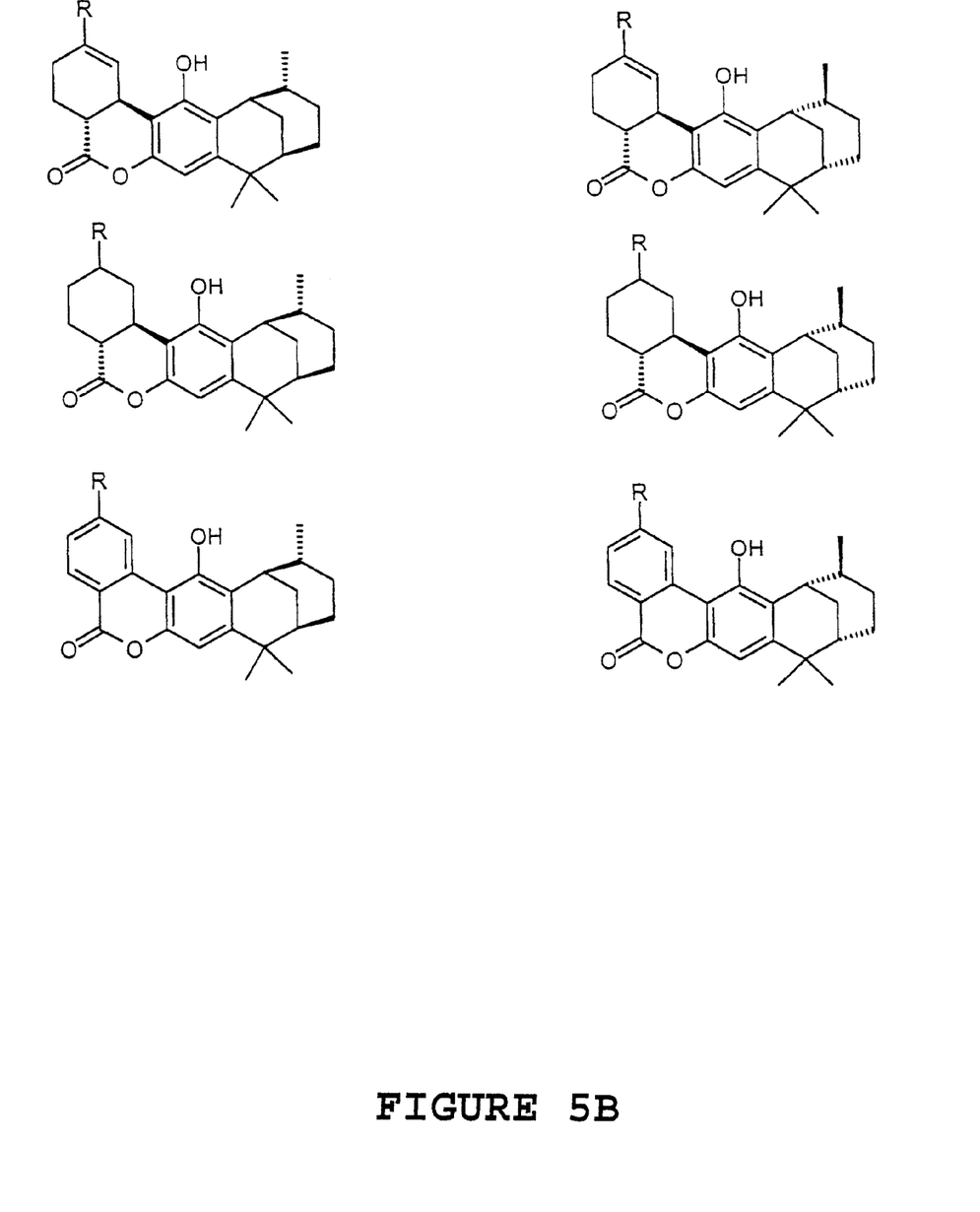
Figure 5C:
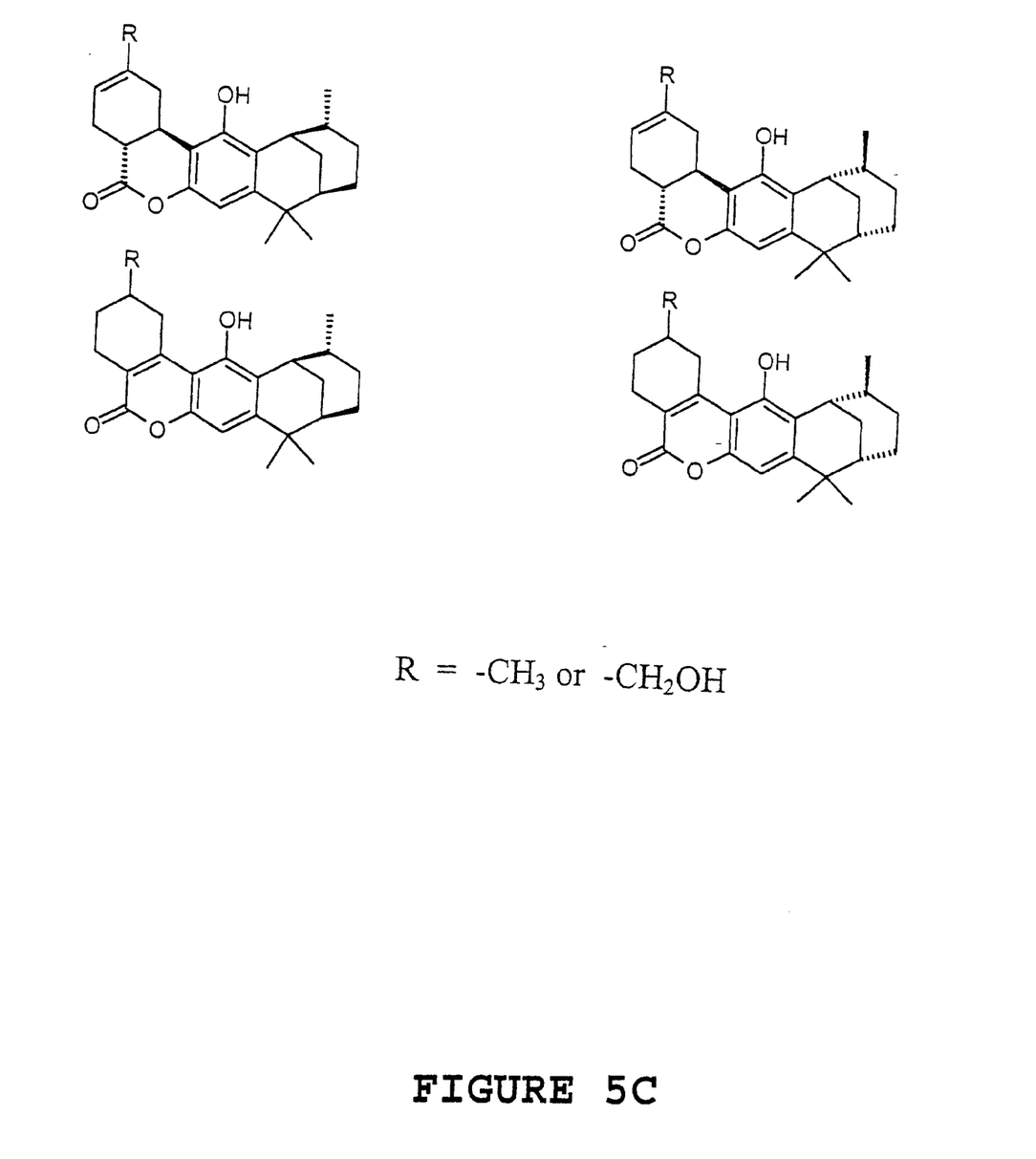

The compounds of the present invention can be prepared according to synthetic methods shown in FIGS. 2–4. Exemplary conditions for these syntheses are provided in Example 1. Deoxy analogs, i.e., compounds in which the hydroxyl group attached to the phenyl ring is replaced by —H, can be prepared by suitable modification of these procedures. For example, deoxy compounds can be prepared by using the appropriate dimethoxy analog in place of compound 1 in the schemes shown in FIG. 2 or a monomethyl recorcinol in place of 2,6-dimethoxyphenol in the schemes shown in FIG. 3.

Also included in the present invention are physiologically acceptable salts of the novel CB2 selective agonists disclosed herein. Salts of compounds containing a phenolic group or other acidic functional group can be prepared by reacting with a suitable base, for example, a hydroxide base or amine base. Salts of acidic functional groups contain a countercation such as sodium, potassium, ammonium and the like. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as choride, bromide, iodide, acetate, perchlorate and the like.

The novel compounds of the present invention have utilities other than immunomodulation. For example, the CB2 selective cannabinoids disclosed herein can be used to screen cells for CB2 receptor expression. The cells are contacted with a radiolabelled CB2 selective cannabinoid, washed to remove unbound compound and then counted to assess retained radioactivity. Cells which retain radioactivity bind the CB2 selective cannabinoids and are therefor likely to express the CB2 receptor. CB2 selective cannabinoids can also be used to identify other compounds which bind to the CB2 receptor. For example, radiolabelled CB2 selective cannabinoids can be used in place of CP-55,940 in the CB2 assay described in Example 2. Radiolabeled cannabinoids can be prepared by, for example, by using tritiated reducing agents in converting compound 7 in FIG. 2 to compound 8.

The invention is illustrated by the following examples which are not intended to be limiting in any way.

EXEMPLIFICATION

Example 1

Preparation of the Compound of the Present Invention

Compound 2. A solution of 1.8 g (7.63 mmol) of the known tetralone 1 in 15 mL of dry THF was cooled in an ice-bath and freshly prepared solution of n-hexylmagnesium bromide (9.20 mmol) was added dropwise. The resulting mixture was stirred at room temperature overnight and then poured into saturated ammonium chloride solution. The product was extracted in diethyl ether, organic extracts were combined, dried and solvents removed by rotary evaporation. The crude product was dissolved in 30 mL of chloroform. About 10 mg of p-toluenesulfonic acid was added and the resulting mixture was stirred at room temperature for 30 min. The reaction mixture was washed with 10% sodium bicarbonate solution, dried, and the chloroform evaporated. The residue was chromatographed on silica gel (10% ethyl ether-petroleum ether) to afford 1.90 g (82%) of pure 2 as a colorless oil.

Compound 3. 1.20 g (3.95 mmol) of the alkene 2 was dissolved in 40 mL of absolute ethanol, 200 mg of 10% Pd on C catalyst was added and the solution was subjected to hydrogenation at room temperature and atmospheric pressure for 2 h. The catalyst was filtered off and the filtrate was rotary evaporated. The residue was purified on a small silica gel column to afford 1.11 g (92%) of compound 3.

Compound 4. A piece of potassium metal 105.5 mg (2.70 mmol) in 4 mL of dry THF was heated to reflux with vigorous stirring and then cooled quickly in an ice bath. To this potassium sand, a solution of 0.7 g (2.29 mmol) of compound 3 in 1 mL of THF was added in one portion under a blanket or argon. The red-color mixture was stirred at room temperature for 24 h and then terminated by addition of small amount of methanol followed by water. After acidification, the reaction mixture was extracted with diethyl ether. Combined ether extracts were dried and ether evaporated to afford an oil which was chromatographed to give 260 mg (45%) of the pure product.

A solution of the above dimethyl ether (250 mg, 0.9 mmol) in dichoromethane was cooled in ice bath under argon and 1.26 mL of a 1 M solution of boron tribromide (2.26 mmol of BBr3) in dichloromethane was added dropwise. The reaction mixture was stirred at room temperature for 2 h and then quenched by cautious addition of water. The organic layer was separated, washed with 10% sodium bicarbonate and dried. Rotary evaporation gave a crude product which was chromatographed on silica gel (50% ethyl ether-petroleum ether) to afford 190 mg (85%) of resorcinol 4.

Compound 5 & 6. 7 mg of p-toluenesulfonic acid was added to the solution of resorcinol 4 (63.3 mg, 0.25 mmol) and 43.6 mg of cis/trans-p-menthedienol (0.28 mmol) in 2.5 mL of chloroform, and the mixture was refluxed for 45 min. The solution was cooled to room temperature, washed with 10% sodium bicarbonate, dried, and evaporated. The residue was chromatographed on silica gel (7% ethyl ether-petroleum ether) to afford 35 mg of tetrahydrocannabinol 5 and 7 mg of tetrahydrocannabinol 6 (combined yield 63%).

Compound 7. A solution of potassium bis(trimethysilyl) amide (2.03 mmol in 5 mL of dry THF) was cooled to −78° C. under argon and a solution of 0.4 g of compound 1 (1.69 mmol) in 1 mL of dry THF was added dropwise. The solution was stirred at 78° C. for 45 min and 0.25 mL of 1-bromopentane (neat) was added. The reaction mixture was allowed to warm slowly to room temperature and stirred overnight. The mixture was poured into saturated ammonium chloride solution and extracted with diethyl ether. Combined ether extracts were dried and ether removed. The residue was chromatographed on silica gel (30% ethyl ether-petroleum ether) to afford 0.38 g (75%) of the alkylated product.

Compound 8. Hydrogenolysis of 7. A solution of 70 mg (0.23 mmol) of 7 in 2.3 mL of absolute ethanol was mixed with 11.5 mg of 10% Pd on C catalyst. A few drops of concentrated hydrochloric acid was added and the mixture was hydrogenated at room temperature and atmospheric pressure for 6 h. At the end of the time period, catalyst was filtered off and ethanol was removed by rotary evaporation. The residue was passed through a short column of silica to afford 63.8 mg (90%) of the desired product.

Demethoxylation. The procedure used in identical to the one described above for the preparation of compound 4. Thus, starting from 370 mg (1.27 mmol) of the trimethoxy compound, 106 mg (43%) of the corresponding dimethoxy compound was obtained.

Demethylation using boron tribromide. Procedure similar to the one described for the preparation of compound 4. Starting from 100 mg (0.38 mmol) of the dimethyl ether, 76.5 mg (86%) of resorcinol 8 was obtained.

Compound 9. Procedure used is similar to the one described for the preparation of compound 5. Starting from 61.6 mg (0.26 mmol) of the resorcinol 8, 59.2 mg (62%) of tetrahydrocannabinol 9 was obtained.

Compound 10. The mixture of 6.50 g of 2,5-dimethoxy phenol (42 mmol) and 7.70 g of (1S, 2S, 3S, 5R)-(+)-isopinocampheol (50 mmol) in 200 ml of 70% methanesulfonic acid was heated and stirred in a 70° C. oil bath for 24 hr. After cooling to room temperature, the reaction mixture was poured onto ice and extracted with methylene chloride. The extracts were washed with water and saturated with sodium bicarbonate solution, dried with sodium sulfate. Removal of solvent provided 15.0 g of brown oil crude. The crude was subjective to multiple column chromatography purification with the elution solvent of the mixture of hexane, methylene chloride and ethyl acetate (5:5:1). The component of Rf value of 0.52 was collected.

Compounds 11 to 13. These three compounds were prepared by the methods described in Dominiami et al., *J. Org. Chem.* 42:344 (1977), the entire teachings of which are incorporated herein by reference.

Compounds 14 and 15. The mixture of 1 mmol of 13, 3 mmol trans-p-mentha-2, 8-dien-1-ol and 36 mg of p-toluenesulfonic acid monohydrate in 10 ml of chloroform was stirred and heated in a 70° C. oil bath for 3 hours. Then the reaction temperature was lowered to room temperature. The reaction was quenched by addition of 5 ml of saturated sodium bicarbonate solution. After separation, the aqueous layer was extracted twice by methylene chloride. The combined organic layer is washed by brine, dried over sodium sulfate. Removal of solvent by vacuum evaporation provided the yellow oil crude product. The products were purified by column chromatography. Elution solvent was the mixture of petroleum ether and ethyl acetate with the ratio of 100 to 3. The yield of 14 was 28%. The yield of 15 was 30%. The melting point of 14 was 72–73° C. The melting point of 15 was 216–217° C.

Compounds in Scheme 4 of FIG. 4. The compounds in scheme 4 of FIG. 4 are synthesized through the methods described in Love et al., *J. Med. Chem.* 16:1200 (1973), Meltzer et al., *Synthesis,* 1981:985 (1981) and Gareau, *Bioorg. Med. Chem. et al.,* 6:189 (1996), the entire teachings of which are incorporated herein by reference.

Example 2

Compounds of the Present Invention Selectively Bind to the CB2 Receptor

Radioligand Binding Assay

The binding affinities of the novel compounds described in this invention for the central cannabinoid receptor were assessed using rat forebrain membranes as a source of CB1. Membranes were prepared as described by the method of Dodd et al., *Brain Res.* 226:107 (1981), the entire teachings of which are incorporated herein by reference. Rat whole brains minus the cerebral cortex were diced with a razor blade and homogenized in 0.32 M sucrose, pH 7.4. The resulting suspension was spun at 400×g at 4° C. The supernatant was decanted and layered over 1.2 M sucrose in TME buffer (25 mM Tris base, 5 mM $MgCl_2$ 1 mMEDTA, pH 7.4) and spun at 109,000×g. The interface containing plasma membrane protein was collected, pooled and layered over 0.8 M sucrose in TME, pH 7.4. The pellet was carefully resuspended in TME, pH 7.4 and the total protein content was assayed by the method of Markwell et al., *Anal. Biochem.* 87:206 (1978), the entire teachings of which are incorporated herein by reference. Protein was aliquotted, frozen under liquid nitrogen and stored at −80° C. until use.

Approximately 30 µg of tissue was incubated in silanized 96 well microtiter plate with TME containing 0.1% essentially fatty acid free bovine serum albumin (BSA), 0.8 nM [$H^3$]CP-55,940 and various concentrations of the test compound in a final volume of 200 µL. Assays were incubated at 30° C. for 1 hour. The samples were filtered using Packard Filtermate 196 and Whatman GF/C Filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations were normalized between 100% and 0% specific binding for [$H^3$]CP-55,940, determined using buffer and 100 nM CP-55,940. The normalized data was analyzed using a 4 parameter nonlinear logistic equation to yield $IC_{50}$ values. Data from at least two independent experiments performed in duplicate were used to calculate $IC_{50}$ values which were convered to $K_i$ values using the assumptions of Cheng and Prusoff, *Biochem. Pharmacol.* 22:3099 (1973), the entire teachings of which are incorporated by reference.

Mouse spleen was used as a source of CB2 receptors to assess binding affinity of analogs described in this invention. The CB2 binding assay was conducted in the same manner as for CB1. Silanized centrifuge tubes were used throughout to minimize receptor loss due to adsorption.

The $K_i$s (nanomolar)for a number of the compounds of the present invention are shown in the Table below:

TABLE

| Compound | $K_i$ in nM for the CB1 Receptor | $K_i$ in nM for the CB2 Receptor |
|---|---|---|
| AM724 | 6877 | 16.9 |
| AM725 | $3.6 \times 10^5$ | 280.5 |
| AM726 | 2018 | 83.2 |
| AM727 | $6.2 \times 10^4$ | 1244 |
| AM856 | 402.4 | 161.5 |
| AM855 | 22.3 | 58.6 |
| AM858 | 524.1 | 455.6 |

As can be seen, a number of compounds have an affinity for the CB2 receptor that is several orders of magnitude greater than for the CB1 receptor.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A compound represented by the following structural formula:

wherein Ring A has zero to three endocyclic double bonds;

X is >C(CH$_3$)$_2$ or —C=O;

R$_1$ is —H, —OH, —OCH$_3$, —OCH$_2$CH$_3$, halogen, —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ or —CH$_2$C(halogen)$_3$; and R$_2$ and R$_3$, taken together with the carbon atoms to which they are bonded, form a substituted or unsubstituted C6 monocyclic or a C7–C10 bicyclic carbocyclic ring.

2. The compound of claim 1 wherein the compound is represented by the following structural formula:

wherein:

R$_1$ is —CH$_3$ or —CH$_2$OH;

R$_4$–R$_7$ are independently —H or a C1 to C10 straight chained substituted or unsubstituted alkyl group; and wherein R$_6$ and R$_7$, taken together, form a substituted or unsubstituted ethylene, propylene or —(CH$_2$)$_4$— group.

3. The compound of claim 2 wherein R$_4$ and R$_5$ are —H or —CH$_3$.

4. The compound of claim 3 wherein the compound is represented by the following structural formula:

wherein R$_8$ is a C1–C4 substituted or unsubstituted alkyl group.

5. The compound of claim 4 wherein the compound is represented by a structural formula selected from:

or

6. A method of suppressing the immune system in a subject comprising administering to the subject a therapeutically effective amount of a compound comprising a tricyclic cannabinoid core and a substituted or unsubstituted C5–C8 carbocyclic ring, a five to eight-membered heterocyclic ring or a seven to ten membered bicyclic ring system, wherein:

a) wherein the tricyclic cannabinoid core comprises a phenyl ring and a six-membered carbocyclic ring fused to a central pyran ring or a central six-membered lactone ring; and b) the substituted or unsubstituted C5–C8 carbocyclic ring, five to eight-membered heterocyclic ring or a seven to ten membered bicyclic ring system is fused to the phenyl ring and physiologically acceptable salts thereof.

7. The method of claim 6 wherein the compound is represented by the following structural formula:

wherein Ring A has zero to three endocyclic double bonds;

X is >C(CH$_3$)$_2$ or —C=O;

R$_1$ is —H, —OH, —OCH$_3$, —OCH$_2$CH$_3$, halogen, —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ or —CH$_2$C(halogen)$_3$; and R$_2$ and R$_3$, taken together with the carbon atoms to which they are bonded, form a substituted or unsubstituted five to eight-membered heterocyclic ring.

8. The method of claim 6 wherein the compound is represented by the following structural formula:

wherein Ring A has zero to three endocyclic double bonds;

X is >C(CH$_3$)$_2$ or —C=O;

R$_1$ is —H, —OH, —OCH$_3$, —OCH$_2$CH$_3$, halogen, —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ or —CH$_2$C(halogen)$_3$; and R$_2$ and R$_3$, taken together with the carbon atoms to which they are bonded, form a substituted or unsubstituted C5–C7 monocyclic, C7–C10 bicyclic carbocyclic ring or a five to eight-membered heterocyclic ring.

9. The method of claim 6 wherein the compound is represented by the following structural formula:

wherein Ring A has zero to three endocyclic double bonds;

X is >C(CH$_3$)$_2$ or —C=O;

R$_1$ is —H, —OH, —OCH$_3$, —OCH$_2$CH$_3$, halogen, —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ or —CH$_2$C(halogen)$_3$; and R$_2$ and R$_3$, taken together, form a substituted or unsubstituted C5–C7 monocyclic or C7–C10 bicyclic carbocyclic ring.

10. The method of claim 9 wherein the compound is represented by the following structural formula:

wherein:

R$_1$ is —CH$_3$ or —CH$_2$OH;

R$_4$–R$_7$ are independently —H or a C1 to C10 straight chained substituted or unsubstituted alkyl group; and wherein R$_6$ and R$_7$, taken together, can form a substituted or unsubstituted ethylene, propylene or —(CH$_2$)$_4$— group.

11. The method of claim 10 wherein R$_4$ and R$_5$ independently are —H or —CH$_3$.

12. The method of claim 11 wherein the compound is represented by the following structural formula:

wherein R$_8$ is a C1–C4 substituted or unsubstituted alkyl group.

13. The method of claim 12 wherein the compound is represented by a structural formula selected from:

or

14. A compound represented by the following structural formula:

wherein Ring A has zero to three endocyclic double bonds;

X is >C(CH$_3$)$_2$ or —C=O;

R$_1$ is —H, —OH, —OCH$_3$, —OCH$_2$CH$_3$, halogen, —CN, —NO$_2$, —CH$_3$, —C(halogen)$_3$, —CH$_2$OH, —CH$_2$OCH$_3$, —CH$_2$OCH$_2$CH$_3$, —CH$_2$(halogen), —CH$_2$CN, —CH$_2$NO$_2$, —CH$_2$CH$_3$ or —CH$_2$C(halogen)$_3$;

R₂ and R₃, taken together with the carbon atoms to which they are bonded, form a substituted or unsubstituted C5 or C8 monocyclic carbocyclic ring.

15. A compound represented by the following structural formula:

wherein Ring A has zero to three endocyclic double bonds;

X is >C(CH₃)₂ or —C=O;

R₁ is —H, —OH, —OCH₃, —OCH₂CH₃, halogen, —CN, —NO₂, —CH₃, —C(halogen)₃, —CH₂OH, —CH₂OCH₃, —CH₂OCH₂CH₃, —CH₂(halogen), —CH₂CN, —CH₂NO₂, —CH₂CH₃ or —CH₂C(halogen)₃; and R₂ and R₃, taken together with the carbon atoms to which they are bonded, form a substituted or unsubstituted five to eight-membered heterocyclic ring.

16. A compound represented by the following structural formula:

wherein Ring A has zero to three endocyclic double bonds;

X is >C(CH₃)₂ or —C=O;

R₁ is —H, —OH, —OCH₃, —OCH₂CH₃, halogen, —CN, —NO₂, —CH₃, —C(halogen)₃, —CH₂OH —CH₂OCH₃, —CH₂OCH₂CH₃, —CH₂(halogen), —CH₂CN, —CH₂NO₂, —CH₂CH₃ or —CH₂C(halogen)₃; and R₂ and R₃, taken together with the carbon atoms to which they are bonded, form a substituted or unsubstituted C5–C7 monocyclic carbocyclic ring, a five to eight-membered heterocyclic ring or a C7–C10 bicyclic carbocyclic ring.

* * * * *